(12) United States Patent
Kemp et al.

(10) Patent No.: US 11,779,721 B2
(45) Date of Patent: Oct. 10, 2023

(54) ORAL SUCTION DEVICE

(71) Applicant: The University of Southern Mississippi, Hattiesburg, MS (US)

(72) Inventors: Lisa Kemp, Hattiesburg, MS (US); Nina McLain, Philadelphia, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 598 days.

(21) Appl. No.: 16/444,855

(22) Filed: Jun. 18, 2019

(65) Prior Publication Data

US 2020/0398008 A1    Dec. 24, 2020

(51) Int. Cl.
| | |
|---|---|
| *A61M 16/04* | (2006.01) |
| *A61B 90/70* | (2016.01) |
| *A61M 1/00* | (2006.01) |
| *A61B 1/267* | (2006.01) |
| *A61L 29/16* | (2006.01) |
| *A61B 5/01* | (2006.01) |

(52) U.S. Cl.
CPC ......... *A61M 16/0463* (2013.01); *A61B 1/267* (2013.01); *A61B 90/70* (2016.02); *A61L 29/16* (2013.01); *A61M 1/84* (2021.05); *A61M 16/0479* (2014.02); *A61B 5/01* (2013.01); *A61M 2205/0238* (2013.01)

(58) Field of Classification Search
CPC ... A61B 7/023; A61M 16/04; A61M 16/0463; A61M 16/0479; A61M 1/84; A61M 2205/0238; A61M 2210/0625
See application file for complete search history.

(56) References Cited

U.S. PATENT DOCUMENTS

| | | | |
|---|---|---|---|
| 3,101,543 | A | 8/1963 | Baughan |
| 3,324,855 | A | 6/1967 | Heimlich |
| 5,919,570 | A | 7/1999 | Hostettler et al. |
| 5,931,831 | A | 8/1999 | Linder |
| 6,460,540 | B1 | 10/2002 | Klepper |
| 6,974,321 | B2 | 12/2005 | Hirsch et al. |
| 7,089,942 | B1 | 8/2006 | Grey |
| 8,196,584 | B2 | 6/2012 | Maguire et al. |
| 8,231,606 | B2 | 7/2012 | Stenzler et al. |
| 8,617,542 | B2 | 12/2013 | Madhyastha et al. |
| 9,457,163 | B2 | 10/2016 | Ward et al. |
| 10,099,027 | B2 | 10/2018 | Cole et al. |
| 2004/0000314 | A1 | 1/2004 | Angel |
| 2007/0017527 | A1 | 1/2007 | Totz |

(Continued)

OTHER PUBLICATIONS

Jelic, S., Cunningham, J.A. & Factor, P. Clinical review: Airway hygiene in the intensive care unit. Crit Care 12, 209 (2008). https://doi.org/10.1186/cc6830.

(Continued)

*Primary Examiner* — Deanna K Hall
(74) *Attorney, Agent, or Firm* — Butler Snow LLP

(57) ABSTRACT

An oral suction device includes a suction catheter having a suction portion at a first end, a sponge surrounding the suction portion, a hydrogel or non-hydrogel polymer coating on the sponge, and a suction tubing connector on a second end opposite the first end. In some aspects the coating is a hydrogel coating that does not have macropores. A method of making an oral suction device may include dip-coating a sponge and forming macropores in the coating during the coating process.

20 Claims, 12 Drawing Sheets

(56) References Cited

U.S. PATENT DOCUMENTS

| | | | |
|---|---|---|---|
| 2007/0044806 A1 | 3/2007 | Madsen et al. | |
| 2007/0225564 A1 | 9/2007 | Couvillon et al. | |
| 2007/0227543 A1 | 10/2007 | Peichel | |
| 2008/0011304 A1 | 1/2008 | Stewart | |
| 2008/0215034 A1 | 9/2008 | Clayton et al. | |
| 2009/0293882 A1 | 12/2009 | Terry | |
| 2009/0319035 A1 | 12/2009 | Terry | |
| 2010/0074932 A1 | 3/2010 | Talsma | |
| 2010/0087789 A1 | 4/2010 | Leeflang et al. | |
| 2011/0015724 A1 | 1/2011 | Köcher et al. | |
| 2011/0022005 A1 | 1/2011 | Köcher | |
| 2011/0137267 A1 | 6/2011 | Phillips et al. | |
| 2012/0310216 A1 | 12/2012 | Koltchine et al. | |
| 2015/0209535 A1* | 7/2015 | Cole | A61M 16/0463 128/202.16 |
| 2019/0083731 A1 | 3/2019 | Cole et al. | |

OTHER PUBLICATIONS

Divatia, Jigeeshu V; Khan, Parvez U; Myatra, Sheila N. Tracheal intubation in the ICU: Life saving or life threatening ?. Indian Journal of Anaesthesia 55(5):p. 470-475, Sep-Oct. 2011. | DOI: 10.4103/0019-5049.89872. https://doi.org/10.4103/0019-5049.89872.

Wayne, G. B. (Mar. 20, 2019). Ineffective Airway Clearance Nursing Care Plan. Nurselabs. https://nurseslabs.com/ineffective-airway-clearance/.

Fletcher, J. (Nov. 15, 2018). Intubation: Everything you need to know. Medical News Today. https://www.medicalnewstoday.com/articles/323696#recovery.

Suctioning. (n.d.). Physiopedia. https://physio-pedia.com/Suctioning.

Clearing the Airway. (Jan. 2004). EMS World. https://www.hmpgloballearningnetwork.com/site/emsworld/article/10324973/clearing-airway.

Say, S. D. (Jan. 17, 2019). What Types of Airway Management Equipment Are There? SSCOR. https://blog.sscor.com/what-types-of-airway-management-equipment-are-there.

Respiratory Management. (n.d.). C. R. Bard. https://www.crbard.com/medical/Professionals/Product-Concentrations/ Respiratory-Management. Retrieved from https://web.archive.org/web/20210506162952/https://www.crbard.com/ medical/Professionals/Product-Concentrations/Respiratory-Management on May 3, 2023.

SonarMedTM Airway Monitoring System. (n.d.) Medtronic. https://www.medtronic.com/covidien/en-US/products/airway- monitoring-systems/sonarmed-airway-monitoring-system.html?sfdcid=70140000001TO71QAG&cid=PPC:GOOG:et% 20tube% 20suctioning:sonarmed&gclid=Cj0KCQjw38- date not given /DKK/DBhDpARIsADJ3kjnmR5N61VFpRYZobFNaSXLWyl1BmQ7Dse9_ooD4LD1B70x9NH5LjFwaAsogEALw_wCB.

Medical Expo (n.d.) https://www.medicalexpo.com/medical-manufacturer/antiviral-filter-47172.html.

Endotracheal intubation. (n.d.) https://medlineplus.gov/ency/article/003449.htm.

CMI. (Apr. 3, 2019). Global Endotracheal Tube Market to Surpass US$ 3.2 Billion by 2026. Coherent Market Insights. https://www.globenewswire.com/news-release/2019/04/03/1796332/0/en/Global-Endotracheal-Tube-Market-to-Surpass-US-3-2-Billion-by-2026-Coherent-Market-Insights.html.

Allied Market Research. (Mar. 9, 2018). Global Coated Endotracheal Tube Market Expected to Reach $2,518 Million by 2023. Cision PR Newswire. https://www.prnewswire.com/news-releases/global-coated-endotracheal-tube-market-expected-to-reach-2518-million-by-2023---allied-market-research-676370353.html.

* cited by examiner

ORAL SUCTION DEVICE

BACKGROUND

Endotracheal intubation is used to provide mechanical ventilation to patients who are unable to breath on their own. A tube is inserted into the trachea through the mouth to maintain an open airway, while a ventilator moves breathable gases in and out of the lungs. Mechanical ventilation requires keeping pressure in the lungs from the ventilator. An inflatable cuff connected to the endotracheal tube and positioned inside the trachea, seals the lungs and allows ventilation. The inflatable cuff also prevents oral secretions from reaching the lungs, when the glottis is kept open due to intubation. The inflatable cuff should provide the proper amount of pressure against the tracheal wall in order to effectively seal the lungs. If the pressure exerted by the inflated cuff is too high, the cuff may cause damage to the trachea. Insufficient pressure may result in insufficient sealing of the trachea, thus allowing aspiration of oral and gastric secretions into the lungs, with may result in ventilator-associated pneumonia. In practice, however, pressure sufficient to prevent all fluids from entering the lungs will cause damage to the trachea.

Oral secretions are produced by salivary glands, whose ducts open into the oral cavity. Salivary glands may produce approximately one liter of oral secretions per day. If oral secretions, potentially containing infectious bacteria, enter the lungs patients are exposed to the risk of contracting life-threatening infections, such as ventilator-associated pneumonia. Removal of oral secretions from intubated patients would reduce the risk of contracting ventilator-associated pneumonia.

Endotracheal tubes having lumen suction tubes for suctioning oral secretions are known. For example, International Application, International Publication Number WO 92/007602, describes an endotracheal tube, which provides gentle suction action to the tracheal wall. The endotracheal tube includes a main lumen, and an inflatable cuff connected to a cuff lumen for inflating and deflating the inflatable cuff. The endotracheal tube also includes a double lumen, which extends parallel inside the wall of the endotracheal tube and ends proximal to a suction eye, located proximal to the inflatable cuff. The double lumen includes a first lumen, and a second lumen, separated by a separation wall. In order to exercise gentle suction, the separating wall terminates approximately 5 mm from the beginning of the suction eye. However, if the cuff does not make a good seal, or when the cuff is deflated to remove the device from the patient's trachea, oral secretions present in the trachea may reach the lungs. Similar devices are described in German Patent No. DE 69126797, and International Applications, International Publication Numbers WO 95/23624, WO 99/38548, and WO 2010/067225.

The device of U.S. Pat. No. 10,099,027 makes use of an oral suction device for the removal of oral secretions. The device includes a shell, having a plurality of holes, coated with a hydrogel that provides gentle contact with the mucosa and maintains the mouth and throat wet, thus avoiding mouth and throat ulcerations and dryness when the device is used on an intubated patient, and can prevent or inhibit the occurrence of ventilator associated pneumonia.

SUMMARY

In a first aspect, the present invention is an oral suction device, comprising a suction catheter having a suction portion at a first end, a sponge connected to the suction portion, a hydrogel coating on the sponge, and a suction tubing connector, on a second end of the suction catheter, opposite the first end. The hydrogel coating does not include macropores.

In a second aspect, the present invention is a method of removing fluids from a patient, comprising applying suction to the oral suction device described above. The oral suction device is within the oral cavity of the patient.

In a third aspect, the present invention is a method of making an oral suction device, including connecting a sponge to a first end of a suction catheter having a first end and a second end, and coating the sponge with a hydrogel. The hydrogel does not have macropores.

In a fourth aspect, the present invention is an oral suction device, including a suction catheter having a suction portion, a sponge, connected to the suction portion, wherein the sponge is radiopaque, a hydrogel coating on the sponge, a suction tubing connector on a first end of the suction catheter, an electronic temperature probe on a second end of the suction catheter opposite the suction tubing connector, an esophageal stethoscope comprising a stethoscope tube having a listening end. The stethoscope tube enters the suction catheter near the suction tubing connector and is located within the suction catheter, a seal, separating the listening end of the esophageal stethoscope from the suction portion, a stethoscope connector on a first end of the stethoscope tube opposite the listening end, and one or more leads in electrical communication with the electronic temperature probe. The hydrogel does not have macropores.

In a fifth aspect, the present invention is a method of making an oral suction device, including connecting a sponge to a first end of a suction catheter having a first end and a second end, coating the sponge with a hydrogel to form a hydrogel coating, and forming macropores in the hydrogel coating during the coating process.

In a sixth aspect, the present invention is a method of making an oral suction device, including connecting a sponge to a first end of a suction catheter having a first end and a second end, coating the sponge with a polymer to form a polymer coating, forming macropores in the polymer coating during the coating process.

In a seventh aspect, the present invention is an oral suction device, including a suction catheter having a suction portion at a first end, a sponge connected to the suction portion, a non-hydrogel silicone coating on the sponge, and a suction tubing connector, on a second end of the suction catheter, opposite the first end. The non-hydrogel silicone coating has macropores.

In a eighth aspect, the present invention is an oral suction device, including a suction catheter having a suction portion at a first end, a sponge connected to the suction portion, a non-hydrogel polymer coating on the sponge, and a suction tubing connector, on a second end of the suction catheter, opposite the first end. The non-hydrogel polymer coating has macropores.

Definitions

"Macropores" refers to pores that have an average diameter larger than 0.1 millimeters.

DETAILED DESCRIPTION

Figure 1:
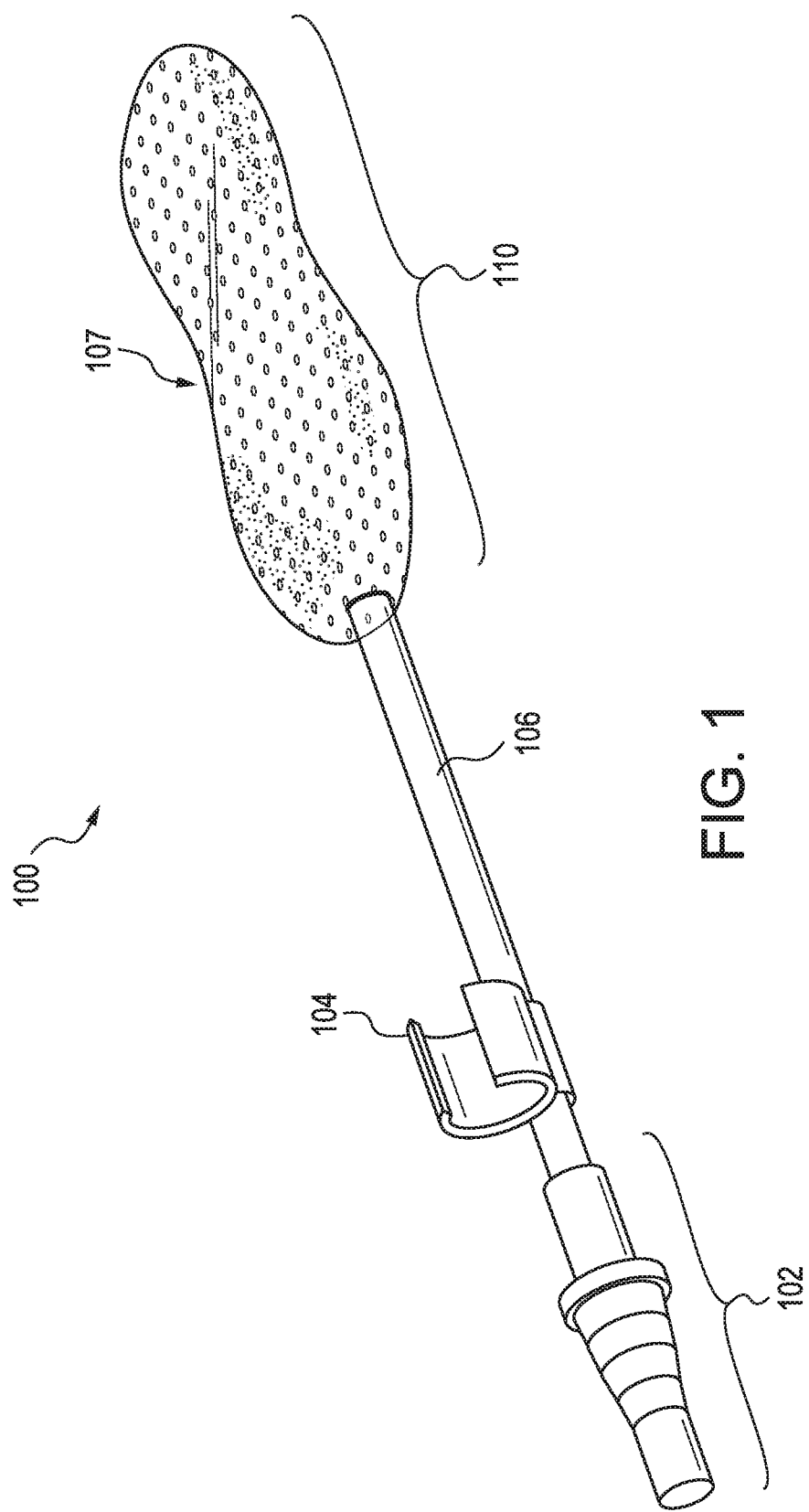
FIG. 1 is a plan view showing an oral suction device.

A problem with using a suction device in a patient's mouth for an extended period of time is that contact between the device and the oral mucosa may cause abrasions and ulcerations in the patient's mouth. Furthermore, removal of oral secretions from the mouth or throat by suction may cause desiccation of the mouth or throat, leading to persistent cough, fungal infections, cavities, periodontitis and ulcers. It is desirable to avoid the onset of such conditions in an intubated patient. The present invention makes use of an oral suction device that includes a hydrogel or non-hydrogel silicone to provide gentle contact with the mucosa and maintains the mouth and throat wet, thus avoiding mouth and throat ulcerations and dryness when the device is used on an intubated patient, and can prevent or inhibit the occurrence of ventilator associate pneumonia. Furthermore, it has also been discovered that providing suction throughout the mouth (both front and back) and in the throat, provides efficient removal of oral secretions. Preferably, the oral suction device suctions away fluids in the oral cavity, the hypopharynx and the supraglotic regions. Since intermittent suction is always on and not dependent on an operator for timing of suction, it will avoid the build-up of fluids and is less expensive to operate. Since the oral suction device may be attached to the endotracheal tube, it is safely fixed in position and may be easily removed.

It is desirable to improve upon the device described in U.S. Pat. No. 10,099,027 ("U.S. Pat. No. '027"). The present invention is based on applying a hydrogel coating onto a sponge without forming macropores in the hydrogel, to improve the manufacturing process by reducing the number of steps, the number of materials, and costs, compared to forming a shell, as described in U.S. Pat. No. '027. Hydrogels allow for absorption through the hydrogel coating, without creating macropores in the hydrogel coating. In another aspect, the device may use a non-hydrogel silicone material to form a coating or shell that surrounds a sponge. After forming the non-hydrogel silicone coating, holes, that is, macropores, are introduced into the coating to allow fluids to contact the sponge so the fluids can be removed from the area. The sponge may be dip coated into the non-hydrogel silicone to form the coating. In another embodiment, a non-hydrogel silicone shell is formed separately from the sponge, and attached to the sponge and/or suction catheter directly.

The thickness of the coating layer may be selected based on the desired rate of fluid removal. A thinner coating will allow the water to be absorbed by the sponge more quickly, than a thicker coating. The selection of the sponge material may impact the thickness of the coating needed to fully coat the sponge, as sponges with larger holes will require a thicker coating to cover the sponge. If the coating applied is not thick enough to fill the holes of the sponge, macropores may form in the coating without manipulating the sponge or coating. Alternatively, macropores may be introduced into the coating after the coating has dried, for example, by poking holes through the coating.

The oral suction device of the present invention includes a suction tubing connector, a sponge and a suction catheter. The device includes a hydrogel coating or a non-hydrogel silicone coating on a sponge. Optionally, the coating may be replaced with a non-hydrogel shell surrounding the sponge. Optionally, the device may include a retention connector, an esophageal stethoscope, and an electronic temperature probe. The oral suction device of the present invention is adapted for placement into a patient's mouth. The shell or coating surrounds the sponge and the sponge is connected to the suction portion of the suction catheter and is positioned within the oral cavity and oropharynx of the patient. Optionally, the device may include an esophageal stethoscope and/or electronic temperature probe, which is inserted in the patient's esophagus. Optionally, a connector may be included, which connects the oral suction device to an endotracheal tube.

FIG. 1 illustrates an oral suction device 100. The oral suction device includes a suction tubing connector 102, which is connected to a suction catheter 106. The suction tubing connector may be connected to an external suction machine (not illustrated). Optionally, a retention connector 104 is connected to the suction catheter, for fixing the location of the oral suction device to an external device, such as an endotracheal tube. A suction end 110 of the oral suction device includes the suction portion (not shown) of the suction catheter 106. The suction end may be oval in shape, or may have an expanded figure-8 shape with a narrow portion 107 in the middle.

Figure 2:
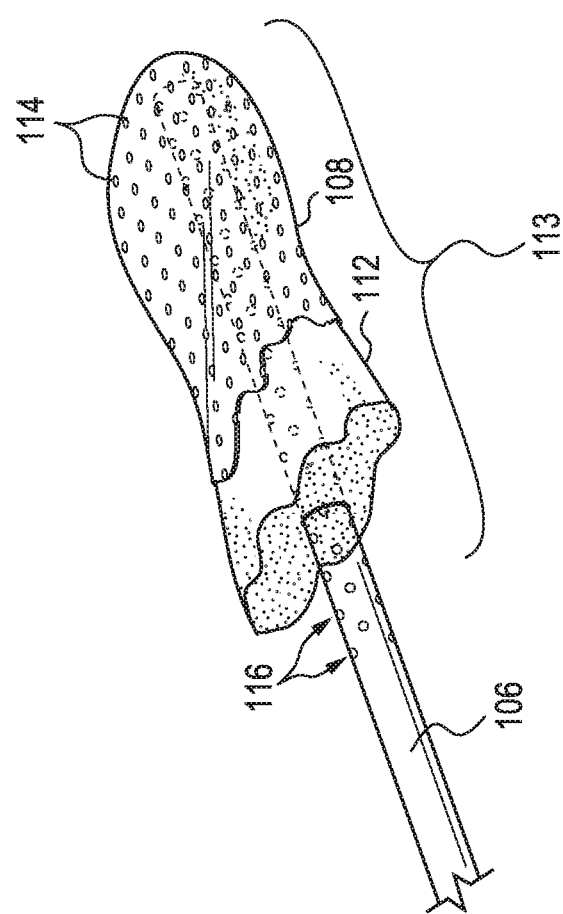
FIG. 2 is a cut away view of an oral suction device.

FIG. 2 illustrates a cut away view of the suction end of an oral suction device. The suction end of the oral suction device includes a non-hydrogel silicone coating or shell 108 surrounding a sponge 112. The sponge surrounds the suction portion 113 of the suction catheter 106. The coating or shell includes a plurality of holes 114 to allow rapid removal of fluids. The suction portion of the suction catheter also includes a plurality of holes 116, in fluid communication with the sponge and holes in the hydrogel, for suctioning fluids.

Figure 3:
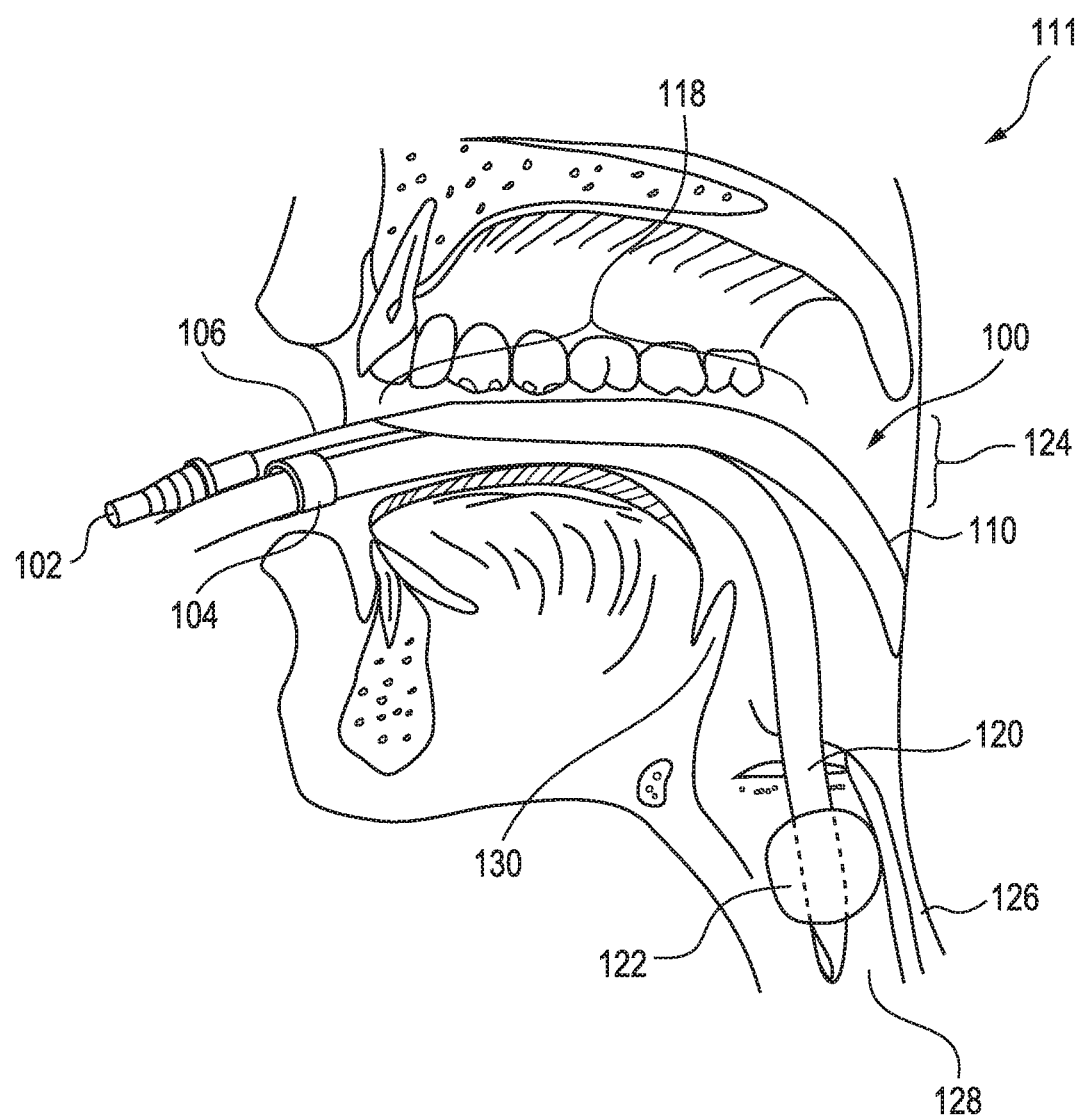
FIG. 3 is a dissection view showing a lateral aspect of a head and neck with an oral suction device.

FIG. 3 illustrates the positioning of the oral suction device 100 in a patient. The illustrations show a cross section of a portion of a patient's head 111, with emphasis on the oral cavity 118, the oropharynx 124, and including the trachea 128, the esophagus 126 and the epiglottis 130; portions of the head and neck have been left out of the illustration for clarity. As shown, the patient is intubated with an endotracheal tube 120 having an inflated endotracheal cuff 122. The suction end 110 of the oral suction device extends from the front of the oral cavity, through the pharyngeal isthmus, into the oropharynx, and preferably makes contact with the back of the throat. The narrower section (107 in FIG. 1) of the suction end of the oral suction device will preferably be located at the pharyngeal isthmus. As illustrated, the retention connector 104 holds the oral suction device to the endotracheal tube. Once positioned within the patient, the suction tubing connector 102 may be connected to an intermittent suction device typically found in an intensive care unit (ICU) of a hospital, so that fluids, such oral secretions, nasal secretions and/or gastric fluids may be removed through the suction catheter 106. Preferably, the oral suction device suctions away fluids in the oral cavity, the hypopharynx and the supraglotic regions.

Suction catheters are flexible plastic tubes, which include an open hole on one end (where they may be attached to the suction tubing connector) and on the opposite end a suction portion having one hole, or optionally having a plurality of holes. Suction catheters including a suction tubing connector are commercially available, for example SAFE-T-VAC™ single suction catheters available from Abbey Medical (Fresno, Calif.), GENTLE FLO™ suction catheters by Covidien available from Health Products Express, Inc. (Boston, Mass.), and french suction catheter with depth markings (MEDLINE DYND 41902) available from Medline industries, Inc. (Mundelein, Ill.). Preferably, the suction catheter has a length of 10 to 40 cm, more preferably 15 to 30 cm, including 16, 17, 18, 19, 20, 21, 22, 23, 24, 25, 26, 27, 28 and 29 cm. Preferably, the suction portion of the suction catheter has a length 0.25 to 0.75 percent of the length of the suction catheter, for example a length of 2.5 to 30 cm, or 4 to 22 cm, including 6, 7, 8, 9, 10, 11, 12, 13, 14, 15, 16, 17, 18, 19 and 20 cm. The number of holes present in the suction portion of the suction catheter is preferably, 6 to 100, more preferably 10 to 60, including 12, 16, 20, 24, 28, 32, 36, 40, 44, 48, 52 and 56 holes. The holes may form a regular pattern, or an irregular pattern. The diameter of the suction catheter is preferably 0.2 to 2 cm, more preferably 0.3 to 1.5 cm, including 0.4, 0.5, 0.6, 0.7, 0.8, 0.9 and 1.0 cm. Preferably, the suction portion of the suction catheter is surrounded by the shell or coating, so that all liquids must pass through the shell or coating during use of the oral suction device. The suction tubing connect is preferably 2 to 10 cm long, more preferably 3 to 8 cm long, including 4, 5, 6 and 7 cm long. The suction tubing connector makes a liquid tight and preferably air tight seal when connected to a suction catheter at an end opposite from the suction portion. The suction tubing connector is adapted to make a fluid tight seal with a flexible and elastic tubing connected to an intermittent suction device.

Preferably, the oral suction device is sterile. Preferably the suction catheter is sterile. Preferably, the sponge is sterile. Preferably, the shell or coating is sterile. Preferably, one or more of the suction catheter, the sponge and the shell or coating are sterile.

Sponges may be cut to the desired size and shape from any surgical or nasal sponge, preferably radiopaque, for example DEROYAL® Surgical Sponges containing an X-ray detectable radiopaque element, available from DeRoyal (Powell, Tenn.). Another example is sponges described in U.S. Pat. No. 7,465,847. The sponge must be large enough to surround the suction portion of the suction catheter. Preferably, the sponge has a length of 3 to 35 cm, or 5 to 25 cm, including 6, 7, 8, 9, 10, 11, 12, 13, 14, 15, 16, 17, 18, 19, 20, 21, 22, 23 and 24 cm. The sponge may be oval in shape or may have an expanded figure-8 shape with a narrow portion in the center. Other shapes are also possible. At the widest point, the sponge has a width of preferably 2 to 8 cm, more preferably 3 to 7 cm, including 4, 5, and 6 cm. At the narrowest point, the sponge is preferably 2 to 8 cm, more preferably 3 to 7 cm, including 4, 5, and 6 cm. The height of the sponge is preferably 0.3 to 4 cm, more preferably 0.4 to 3.5 cm, including 0.5, 0.6, 0.7, 0.8, 0.9, 1.0, 1.2, 1.4, 1.5, 1.6, 1.8, 2.0, 2.5 and 3.0 cm high. The sizing of the sponge is based on the size after the suction catheter is placed inside it. Furthermore, the sponge may be monolithic, or may be composed of 2, 3, 4 or more separate sponges. Sponges with larger pores are preferred, for example 20 or 30 pores per inch. The sponge may be attached to the end of the suction portion, rather than surrounding the suction portion.

Figure 4A:
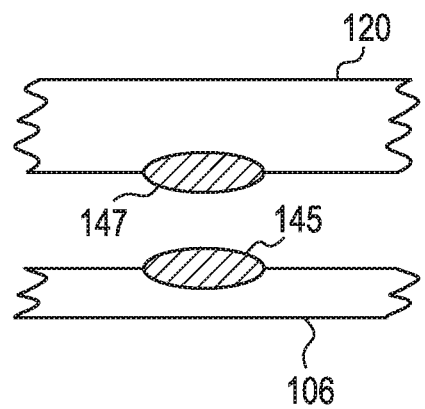
FIGS. 4A and 4B illustrate retention connectors.
Figure 4B:
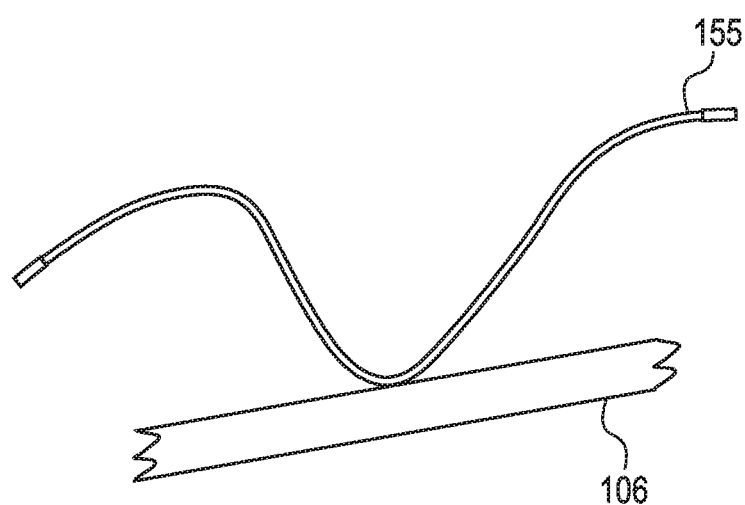

A retention connector may be a C-clip, made of metal or preferably plastic, as illustrated in FIG. 1. Alternatively, the retention connector may be a magnet 145 attached to the suction catheter 106, which mates by magnetic force to a similar magnet 147 attached to the endotracheal tube 120, as illustrated in FIG. 4A. In another alternative, the retention connector may be a string 155 attached to the suction catheter 106, as illustrated in FIG. 4B. The retention connector may be glued, for example with an adhesive, preferably a biocompatible adhesive such as LOCTITE® medical device adhesive, available from Henkel Corporation (Rocky Hill, Conn.), to the suction catheter; similarly the magnets 145 and 147 may be attached to the suction catheter and endotracheal tube, respectively, with an adhesive or biocompatible adhesive. Preferably, the oral suction device is attached to an endotracheal tube during use. In further alternative, the retention connector, such as the C-clip, may be formed as an integrated piece with the suction catheter, to form a monolithic structure.

The hydrogel coating on the sponge may contain one or more hydrogels. The hydrogel materials contain a polymer, have a high-water content, are soft, and are biocompatible (that is, they do not irritate mucosal tissue when in contact for long periods of time, for example 1 hour, 1 day or 1 week). Examples of hydrogel materials include polyacrylamide, polyvinyl pyrrolidone (PVP), silicone hydrogels, polyurethanes (such as thermoplastic polyurethanes) and hydrogels used in contact lenses (for example tefilcon, hioxyfilcon A, lidofilcon, omafilcon A, hefilcon C, phemfilcon, methafilcon A and ocufilcon D) and mixtures thereof. Other examples include polymers and co-polymers of 2-hydroxyethylmethacrylate, glycerol methacrylate, methyl methacrylate, N-vinyl pyrrolidone, N-vinyl-2-pyrrolidone, 2-methacryloyloxyethyl phosphorylcholine, ethoxyethyl methacrylate and methacrylic acid. The hydrogel will also contain water, and may contain one or more salts such as sodium chloride, buffers, preservatives, plasticisers and polyethylene glycol. Methods of making and materials for hydrogels are well known. See for example: Maldonado-Codina, C., "Hydrogel lenses—materials and manufacture: a review" *Optometry in Practice,* 4: 101-15 (2003); Jones et al., "Silicone hydrogel contact lens materials update" (July 2004), available online at www.siliconehydrogels.org/editorials/index_july.asp and www.siliconehydrogels.org/editorials/index_august.asp; and Benz Research & Development (BRD), "Advanced lens materials & manufacture technology", available online at www.benzrd.com/pdf/Advanced Lens Materials 08.pdf. Examples of hydrogel thermoplastic polyurethanes (TPUs) include TECOPHILIC® thermoplastic polyurethanes. These TPUs offer an aliphatic, hydrophilic polyether-based resin which has been specially formulated to absorb equilibrium water contents from 20 to 1000% of the weight of dry resin. Examples of TPUs include TECOPHILIC® SP-80A-150 ("SP-80A-150") and TECOPHILIC® Hydrogel TG-500 (TG-500"), manufactured by LUBRIZOL®.

The hydrogel coating may be formed on the sponge by forming a solution containing the hydrogel. The hydrogel may be introduced into a solvent, such as isopropanol, water, or a combination of isopropanol and water. A sponge, connected to a suction portion of a suction catheter may be covered with the hydrogel solution, to form a coating on the sponge. For example, the hydrogel coating may be formed on the sponge by dip-coating. The coating process may be repeated to increase the thickness and/or weight of the hydrogel coating. This hydrogel coating is permeable to water, so that fluids may be removed from a patient, where the fluid passes through the hydrogel coating and into the sponge. The fluids may be removed from the patient via the suction catheter without the need for macropores.

Alternatively, the coating or shell may be formed of a non-hydrogel silicone material. Silicones consist of an inorganic silicon-oxygen backbone chain with organic side groups attached to the silicon atoms. Silicones have in general the chemical formula $[R_2SiO]_n$, where R is an organic group such as an alkyl or phenyl group. Non-hydrogel silicone may be coated onto a sponge, forming a coating on the sponge. Holes may be introduced into the sponge. Optionally, the silicone may be used to form a shell, having holes, and the shell may be attached to the suction portion. Optionally the shell or coating may be formed from any medical-grade polymer approved for body contact. Examples of suitable plastics and polymers include acetal copolymer, acetal homopolymer, polyethylene teraphthalate polyester, polytetrafluoroethylene, ethylene-chlorotrifluoro-ethylene, polybutylene terephthalate-polyester, polyvinylidene fluoride, polyphenylene oxide, polyetheretherketone, polycarbonate, polyethylenes, polypropylene homopolymer, polyphenylsulfone, polysulfone, polyethersulfone, and polyarylethersulfone.

The coating, the shell and/or the sponge may be impregnated with one or more antibiotics. Examples of antibiotics include cephalosporines such as ceftriaxone, ceftazidime and cefepime; fluoroquinolones such as ciprofloxacin, levofloxacin and moxifloxacin; β-lactams such as ampicillin, sulbactam, piperacillin, tazobactam, ticarcillin, clavulanate and ureidopenicillin; carbapenems such as ertapenem, imipenem and meropenem; glycopeptides such as vancomycin; oxazolidinones such as linezolid; and aminoglycosides such as gentamicin, amikacin and tobramycin; and mixtures thereof. Alternatively, one or more of these antibiotics, and mixtures thereof, may be administered as a liquid or spray into the patient's mouth, so that it will coat the oral cavity and/or the oropharynx, before being suctioned away by the oral suction device.

The shell must be large enough to surround the suction portion of the suction catheter, or if an optional sponge is present, surround the sponge. Furthermore, the shell may be fixed to the suction catheter or the optional sponge simply by being wrapped around it, or by an adhesive, preferably a biocompatible adhesive such as LOCTITE® medical device adhesive, available from Henkel Corporation (Rocky Hill, Conn.). Preferably, the shell has a length of 3 to 35 cm, or 5 to 25 cm, including 6, 7, 8, 9, 10, 11, 12, 13, 14, 15, 16, 17, 18, 19, 20, 21, 22, 23 and 24 cm. The shell may be oval in shape or may have an expanded figure-8 shape with a narrow portion in the center (as illustrated in FIG. 1). Other shapes are also possible. At the widest point, the shell has a width of preferably 2 to 8 cm, more preferably 3 to 7 cm, including 4, 5, and 6 cm. At the narrowest point, the shell is preferably 2 to 8 cm, more preferably 3 to 7 cm, including 4, 5, and 6 cm. The height of the shell is preferably 0.3 to 4 cm, more preferably 0.4 to 3.5 cm, including 0.5, 0.6, 0.7, 0.8, 0.9, 1.0, 1.2, 1.4, 1.5, 1.6, 1.8, 2.0, 2.5 and 3.0 cm high. The sizing of the shell is based on the size after the suction catheter is placed inside it, or when a sponge is present, after the sponge is inside it. When a sponge is used, the shell may preferably have a thickness of 0.01 to 3 cm, more preferably 0.05 to 2 cm, including 0.1, 0.2, 0.3, 0.4, 0.5, 0.6, 0.7, 0.8, 0.9 and 1 cm. When the shell is not a hydrogel, the shell contains a plurality of holes. The number of holes present in the shell is preferably 10 to 10,000, more preferably 100 to 1000.

Figure 5:
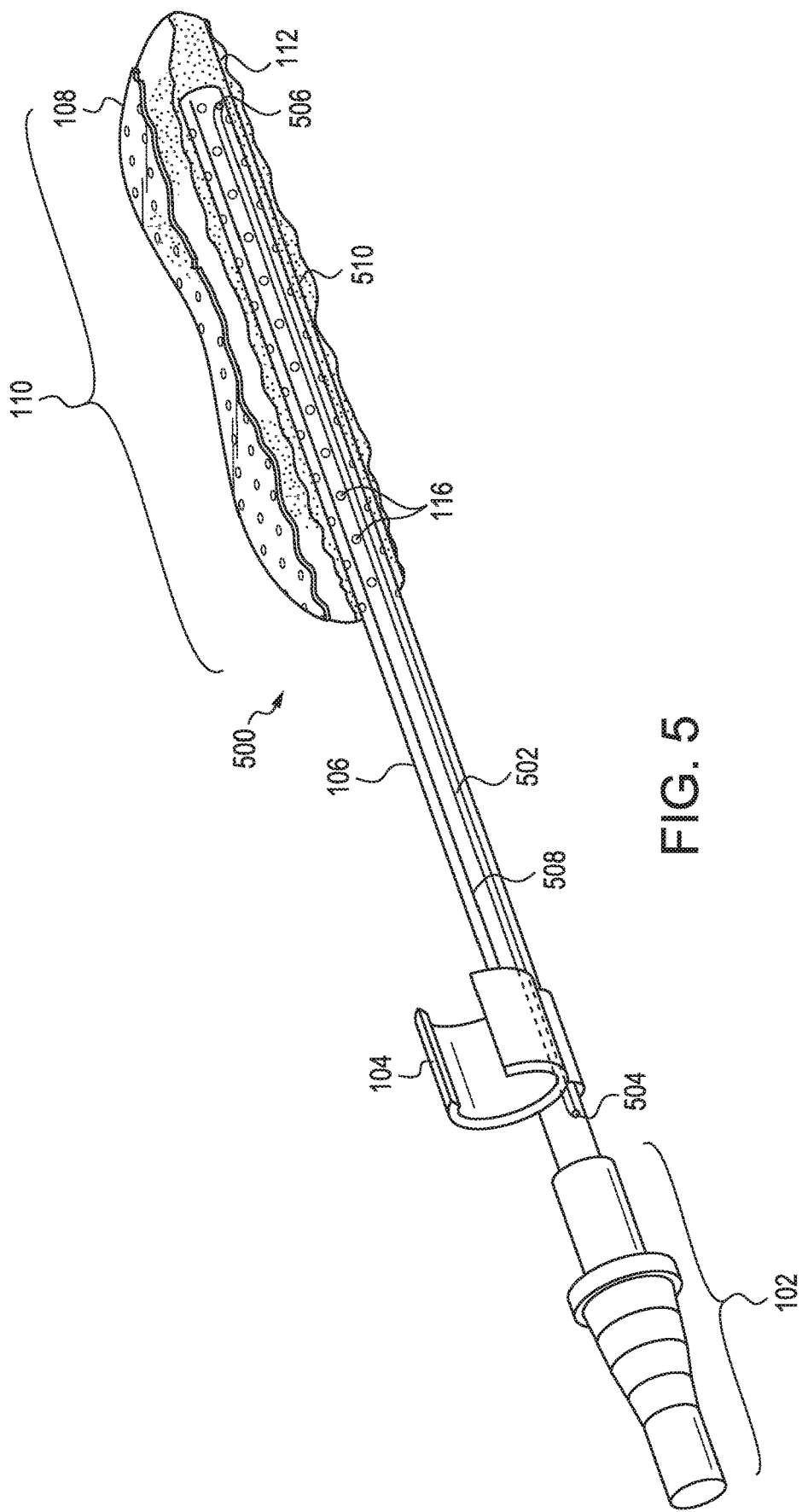
FIG. 5 shows an oral suction device including a vacuum lock relief tube.

FIG. 5 illustrates an oral suction device 500 including a vacuum lock relief tube; the suction end 110 of the oral suction device 600 is illustrated as a cut-away to show details of the interior of the suction end. The oral suction device includes suction catheter 106 connected to a suction tubing connector 102, and a retention connector 104 connected to the suction catheter. The suction portion of the suction catheter, including holes 116 is surrounded by an optional sponge 112, and surrounded by a shell 108. Also present is a vacuum lock relief tube 502, inside the suction catheter, which extends from suction end of the suction catheter, to a point between the suction end of the suction catheter and the retention connector. A first end 504 of the vacuum lock relief tube exits through the wall of the suction catheter, and a second end 506 of the vacuum lock relief tube also exits through the wall of the suction catheter, from within the suction end of the oral suction device. In this way the vacuum lock relief tube creates a gas pathway between the atmosphere and the inside of the sponge or shell. If some of the holes in the suction portion of the suction catheter are blocked, for example by thick mucus, the amount of suction pulling through the remaining holes and the holes in the shell nearby may be great enough to hold tissue from inside the patient's oral cavity or oropharynx tightly against the oral suction device, creating a "vacuum lock" blocking the flow of fluids into the oral suction device. The vacuum lock relief tube prevents the creating of a vacuum lock, by allowing atmospheric air from outside the patient's mouth to enter into the sponge and shell. As illustrated an optional radiopaque element 508 is present in the suction catheter, and an optional radiopaque element 510 is present in the sponge. The radiopaque element may optionally be present in all embodiments.

Figure 6:
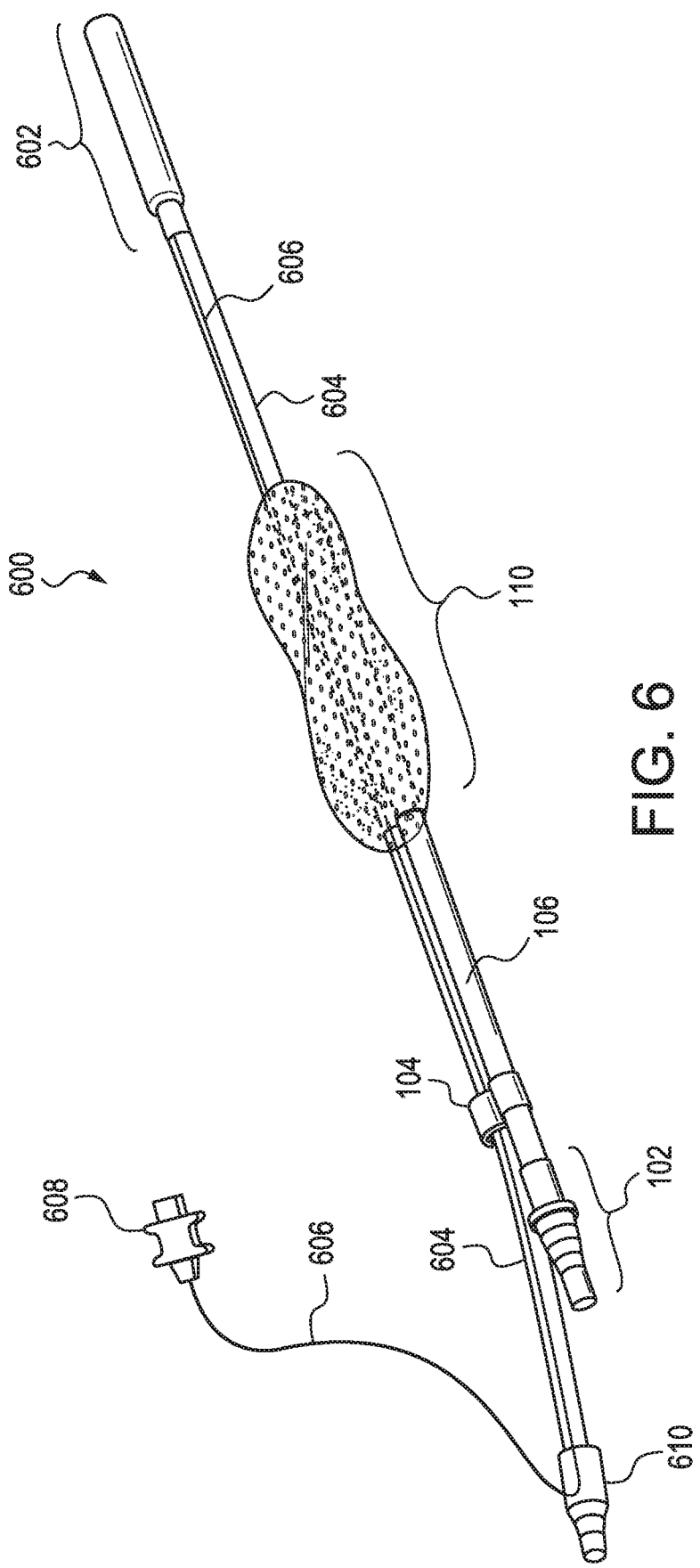
FIG. 6 shows an oral suction device including an esophageal stethoscope and electronic temperature probe.

FIG. 6 illustrates an oral suction device 600 including an esophageal stethoscope and an electronic temperature probe. The oral suction device includes a suction catheter 106 connected to a suction tubing connector 102, and a retention connector 104 connected to the suction catheter, while the suction portion (not illustrated) of the suction catheter is inside the suction end 110 of the oral suction device. An electronic temperature probe 602 is located at a first end of a lead tube 604 which passes through the suction end of the oral suction device, approximately parallel to the suction catheter. Leads 606, which electrically connect the electronic temperature probe with a monitoring device (not illustrated), pass through the lead tube, and may exit the lead tube through an optional lead seal 610. The ends of the leads may be connected to an optional lead adaptor 608, which is adapted for mating with a complementary socket on a monitoring device, for completing the electrical connections between the electronic temperature probe and the monitoring device. The lead tube functions as the esophageal stethoscope and transmits heart and respiratory sounds for auscultation.

The optional esophageal stethoscope and electronic temperature probe may be connected to the suction catheter via the retention connector located on the lead tube. The esophageal stethoscope and electronic temperature probe may be placed in the patient's mouth with the distal tip positioned just above the gastroesophageal junction in the distal portion of the esophagus. The esophageal stethoscope allows auscultation of a patient's heart tones, rates and rhythms, and the electronic temperature probe allows monitoring the patient's core temperature. An example of an esophageal stethoscope and electronic temperature probe is the LIFE-SOUND™ esophageal stethoscope available from NOVAMED USA (Elmsford, N.Y.).

Figure 7A:
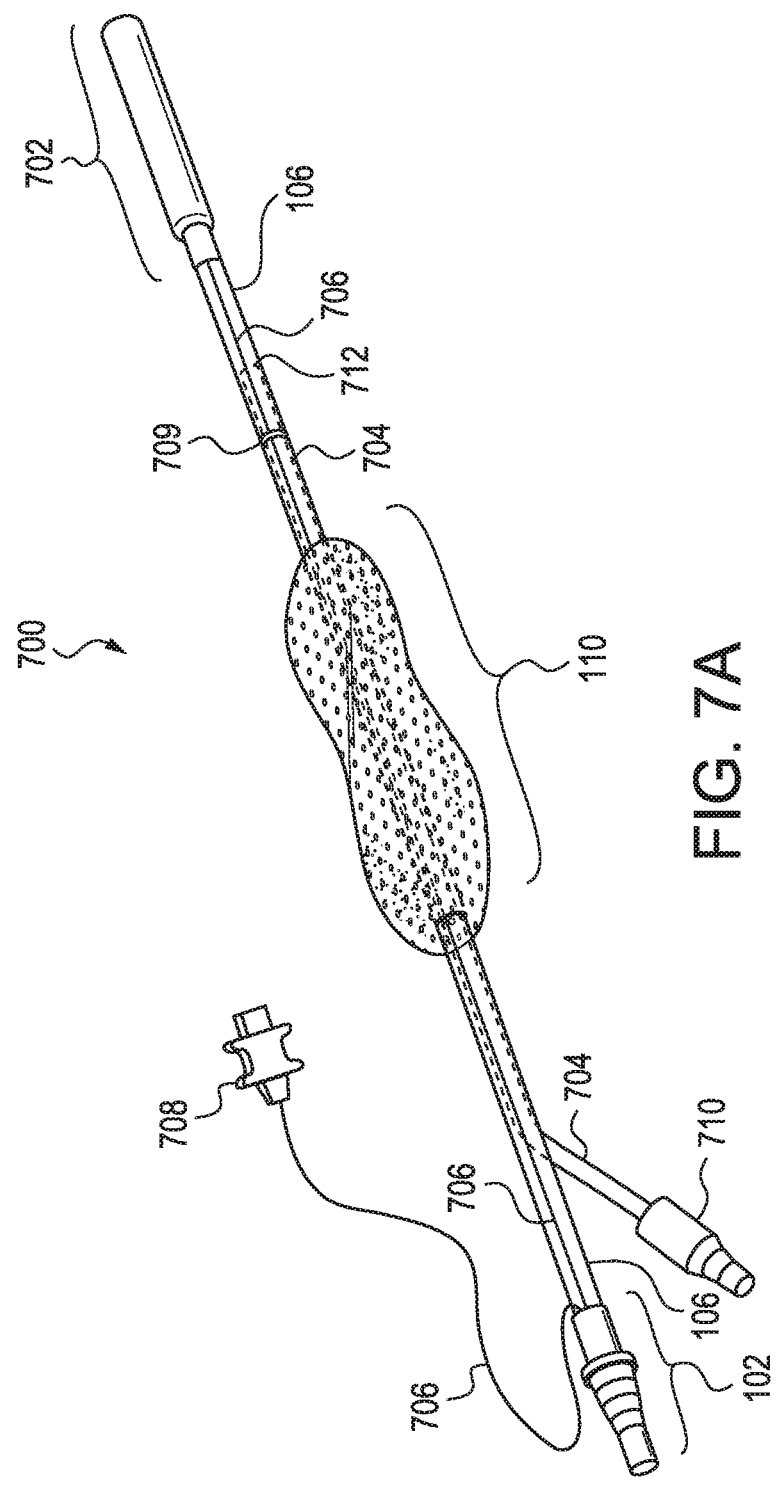
FIG. 7A shows an alternative oral suction device including an esophageal stethoscope and electronic temperature probe.
Figure 7B:
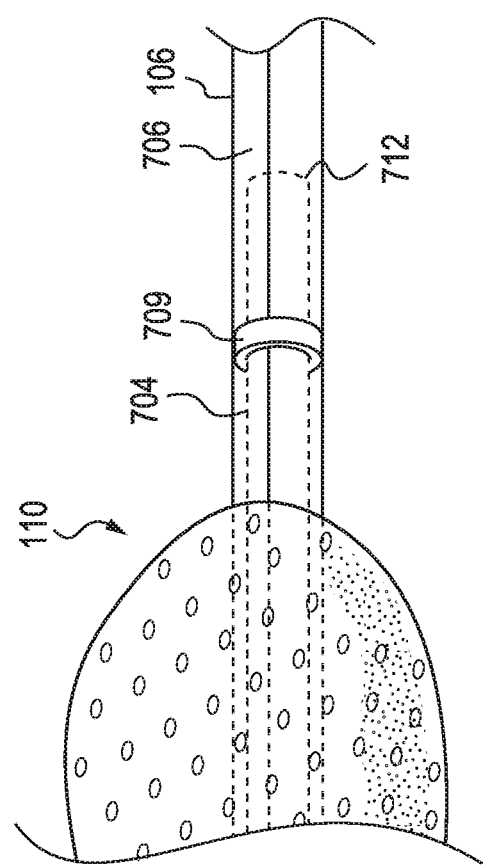
FIG. 7B shows a close up of the alternative oral suction device including an esophageal stethoscope and electronic temperature probe shown in FIG. 7A.

FIG. 7A illustrates an alternative oral suction device 700 including an esophageal stethoscope and an electronic temperature probe. The oral suction device includes a suction catheter 106 connected to a suction tubing connector 102, while the suction portion (not illustrated) of the suction catheter is inside the suction end 110 of the oral suction device. An electronic temperature probe 702 is located at the opposite end of the suction catheter from the suction tubing connector. Leads 706, which electrically connect the electronic temperature probe with a monitoring device (not illustrated) pass through the suction catheter and may exit the suction catheter at the suction tubing connector. The ends of the leads may be connected to an optional lead adaptor 708, which is adapted for mating with a complementary socket on the monitoring device, for completing the electrical connections between the electronic temperature probe and the monitoring device. An esophageal stethoscope includes a stethoscope tube 704 with an isolated listening end 712. The stethoscope tube is connected to a stethoscope connector 710 and enters the suction catheter near the suction tubing connector. The stethoscope tube is located within the suction catheter with the listening end located between the suction end of the suction catheter and the electronic temperature probe. The listening end of the stethoscope is isolated from the suction by a stethoscope seal 709, which improves auscultation by reducing background noise caused by the suction. The stethoscope seal may be formed using a biocompatible sealant such as LOCTITE® medical device adhesive.

In the alternative oral suction device shown in FIG. 7A, the diameter of the stethoscope tube must be smaller than the diameter of the suction catheter. Preferably, the diameter of the stethoscope tube is about half the diameter of the suction catheter. For example, the suction catheter may have a diameter of 6 mm (18 French) and the stethoscope tube may have a diameter of 3 mm (9 French). This design is particularly useful for anesthesiology use.

FIG. 78 illustrates a close-up view of the listening end 712 of the esophageal stethoscope illustrated in FIG. 7A. The stethoscope seal 709 surrounds the stethoscope tube 704 to isolate the listening end of the esophageal stethoscope from the suction. The stethoscope seal may be located at any point along the stethoscope tube between the suction end 110 (partially illustrated) and the electronic temperature probe (not illustrated) to vary the length of the listening end. Leads 706 pass through the stethoscope seal but do not interfere with the noise isolation provided by the stethoscope seal. The stethoscope tube, leads, and stethoscope seal are all located within the suction catheter 106.

Figure 8:
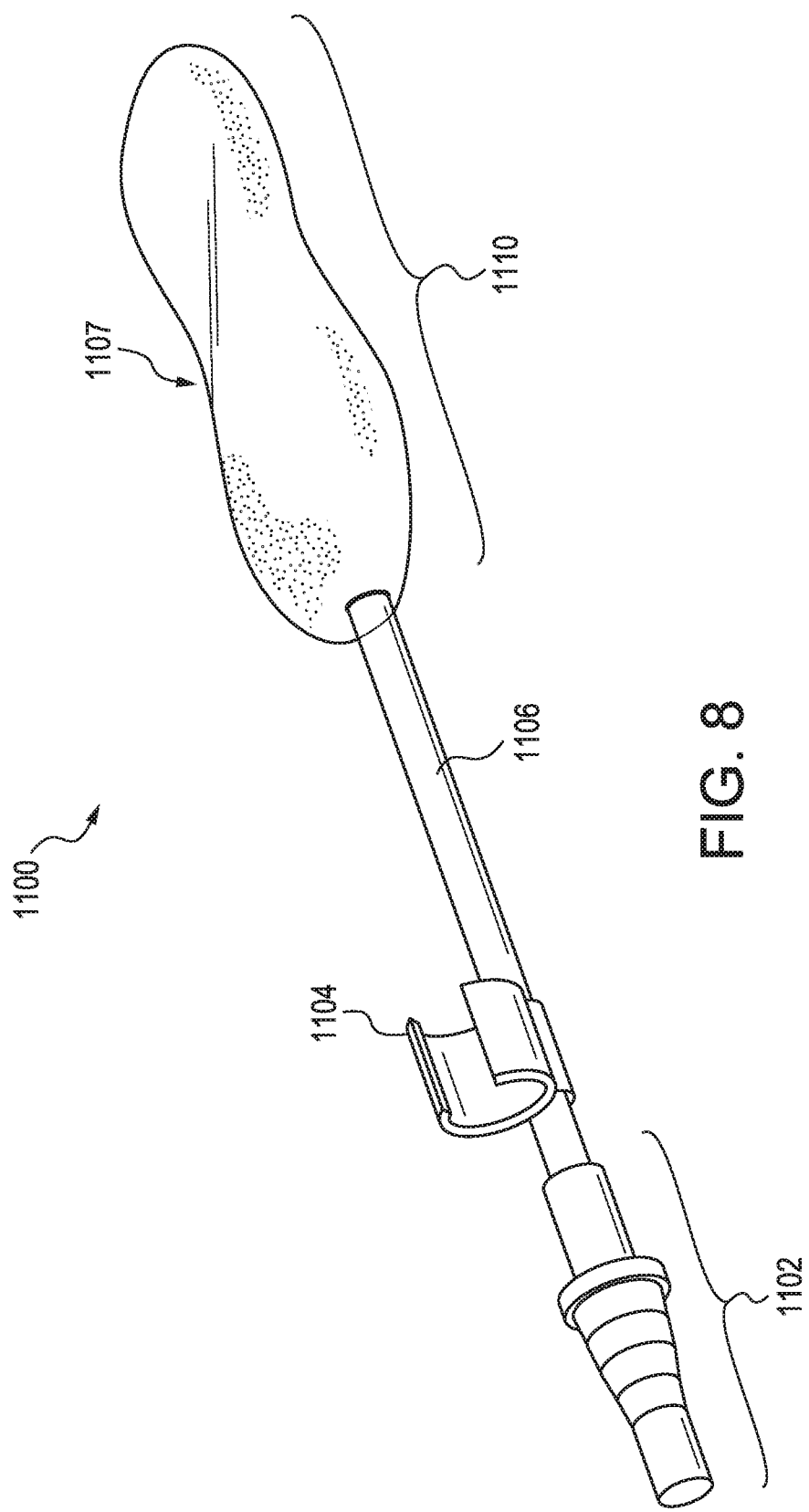
FIG. 8 is a plan view showing an oral suction device without macropores.

FIG. 8 illustrates an oral suction device 1100. The oral suction device includes a suction tubing connector 1102, which is connected to a suction catheter 1106. The suction tubing connector may be connected to an external suction machine (not illustrated). Optionally, a retention connector 1104 is connected to the suction catheter, for fixing the location of the oral suction device to an external device, such as an endotracheal tube. A suction end 1110 of the oral suction device includes the suction portion (not shown) of the suction catheter 1106. The suction end may be oval in shape, or may have an expanded figure-8 shape with a narrow portion 1107 in the middle.

Figure 9:
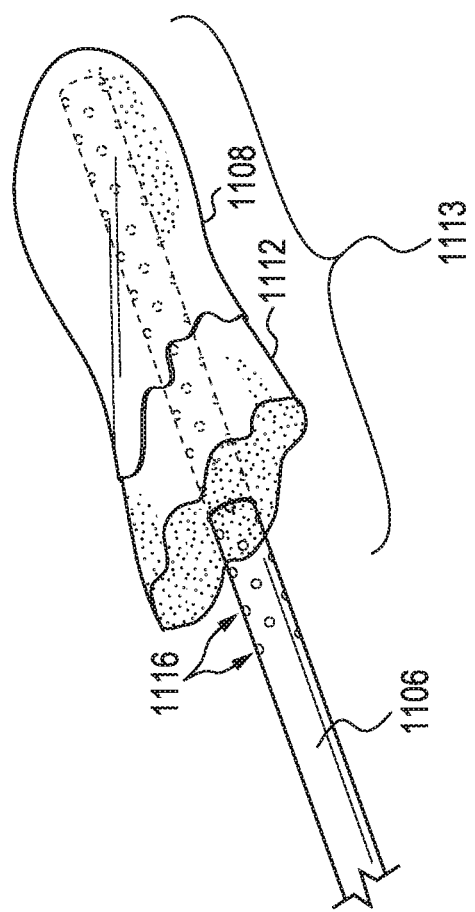
FIG. 9 is a cut away view of an oral suction device without macropores.

FIG. 9 illustrates a cut away view of the suction end of an oral suction device. The suction end of the oral suction device includes a coating 1108 surrounding a sponge 1112. The sponge surrounds the suction portion 1113 of the suction catheter 1106. The coating is a hydrogel coating, and fluids are able to pass through the coating to contact the sponge 1112.

The oral suction device may be used on a patient under general anesthesia in a hospital's ICU. The oral suction device may be used on a patient undergoing surgery, or may be used on a patient post-surgery. The oral suction device may also be used, for example, on a trauma patient at the location where the trauma occurred, after the patient has been partially or fully sedated. If used on a patient who is not under general anesthesia, it may be desirable to apply a local anesthetic to the patient's throat before inserting the oral suction device.

In use, the suction end of the oral suction device is inserted in the patient's oral cavity, as illustrated in FIG. 3. The suction tubing connector is then connected to a suction device, preferably an intermittent suction device (such as the PUSH-TO-SET™ Digital Intermittent Suction Unit available from Ohio Medical Corporation (Gurnee, Ill.)), via a flexible elastic tubing. The oral suction device may then be connected to an endotracheal tube with the retention connector. The oral suction device will then remove fluids, during periods of suction, such as oral secretions, nasal secretions and/or gastric fluids, to prevent or inhibit ventilator-associate pneumonia. Medically trained personnel may determine the interval between suctioning and the duration of suctioning needed. Intermittent suctioning avoids the need of an operator, for example a nurse, to be present when suctioning is needed.

EXAMPLES

Intubated Patient in ICU (Prophetic Example)

Patient #1, age 72, suffering chronic obstructive pulmonary disease (COPD) is hospitalized and taken to the ICU, where the patient is administered general anesthesia and is intubated. After the patient has been sedated, medical personnel introduce an endotracheal tube through the patient's mouth and into the trachea. The cuff connected to the endotracheal tube is inflated to avoid gases from the ventilator escaping from the lungs and refluxing into the trachea. The endotracheal tube is connected to a ventilator. An oral suction device is introduced through the patient's mouth, positioning the suction portion such that half is in the patient's oral cavity and the other half in the patient's oropharynx. The oral suction device is connected to the endotracheal tube via the retention connector. Correct positioning of the oral suction device is confirmed by X-ray imaging of the patient's head, as the oral suction device includes a radiopaque sponge. The oral suction device is connected to an external device which provides intermittent suction. After three weeks, the patient's condition has been stabilized and the oral suction device and the endotracheal tube are removed. The patient is released and does not develop ventilator-associated pneumonia.

Intubated Patient Under Anesthesia (Prophetic Example)

Patient #2, age 32, is hospitalized and taken to the operating room for surgery, where the patient is administered general anesthesia and is intubated. After the patient has been sedated, medical personnel introduce an endotracheal tube through the patient's mouth and into the trachea. The cuff connected to the endotracheal tube is inflated to avoid gases from the ventilator escaping from the lungs and refluxing into the trachea. The endotracheal tube is connected to a ventilator. An oral suction device with an esophageal stethoscope and an electronic temperature probe is introduced through the patient's mouth, positioning the suction portion such that half is in the patient's oral cavity and the other half in the patient's oropharynx, and positioning the electronic temperature probe such that the distal tip is just above the gastroesophageal junction in the distal portion of the esophagus. The suction catheter of the oral suction device is an 18 French tube. The stethoscope tube is located within the suction catheter and is a 9 French tube. The listening end of the stethoscope is isolated from the suction by a stethoscope seal so that the suction noises do not interfere with monitoring the patient's heart sounds. The oral suction device is connected to the endotracheal tube via the retention connector. An earpiece is connected to the stethoscope connector, and hearing the patient's heart tones confirms correct placement of the electronic temperature probe. The oral suction device is connected to an external device which provides intermittent suction. The leads for the electronic temperature probe exit the suction catheter near the retention connector and are connected to a lead adapter, which connects the electronic temperature probe to a monitoring device. During the surgery, the patient's heart tones, heart rates, and heart rhythms are monitored through the esophageal stethoscope without interference from the suction. The patient's core temperature is monitored by the electronic temperature probe. After the surgery is complete, the oral suction device with the esophageal stethoscope and the electronic temperature probe and the endotracheal tube are removed. The patient is transferred to a recovery room and later released from the hospital. The patient does not develop ventilator-associated pneumonia.

Preparation of Oral Suction Devices

A coating mixture was prepared by mixing isopropyl alcohol ("IPA" or "isopropanol") and water in a 500 mL Erlenmeyer flask in a mixture of 90/10%, respectively. A hydrogel was then added to the solution at 10% weight, heated to 60° C., and stirred continuously until a homogenous mixture was formed. The two hydrogels tested were TECOPHILIC® SP-80A-150 ("SP-80A-150") and TECOPHILIC® Hydrogel TG-500 (TG-500").

The ASTM D2369 method was used to determine the volatile content of the coatings for each of the hydrogels. This test method is the procedure of choice for determining volatiles in coatings for the purpose of calculating the volatile organic content in coatings under specified test conditions. The weight percent solids content (nonvolatile matter) may be determined by difference between the original weight and final weight. The percent of volatile content in the solution affects the length of the drying time needed to achieve a solvent-free coating.

To determine the volatile content of various hydrogel samples, 0.3-0.5 g of each hydrogel was spread evenly across the surface of an aluminum weigh boat. The weigh boats were placed in an oven at 110° C. for one hour. After removal from the oven the samples are reconditioned in a desiccator overnight. The weight of the samples was recorded and used to calculate the volatile content of the hydrogel IPA/water mixture.

TABLE 1 volatile content of SP-80A-150 IPA/water mixture

| Sample | Solid Content | Volatile Content |
| --- | --- | --- |
| 1 | 10.40987% | 89.59013% |
| 2 | 10.06025% | 89.93975% |
| 3 | 10.30459% | 89.93975% |
| 4 | 9.851791% | 90.14821% |
| 5 | 9.532325% | 90.46768% |
| 6 | 9.75409% | 90.24591% |

TABLE 2 volatile content of TG-500 IPA/water mixture

| Sample | Solid Content | Volatile Content |
| --- | --- | --- |
| 1 | 11.36494% | 88.63506% |
| 2 | 10.64696% | 89.35304% |
| 3 | 11.88481% | 88.11519% |
| 4 | 15.59802% | 84.40198% |
| 5 | 11.54923% | 88.45077% |
| 6 | 7.63786% | 92.36214% |

Dry sponge samples were weighed and recorded. Samples were then dipped into the hydrogel IPA/water mixture and wiped on the edges of the jar to reduce dripping into the oven. Samples were hung by a clothes hanger in the oven at 90° C. for 1 hour. The samples were then reconditioned before recording the weight. The sponge weight, prior to the coating, is shown in Table 3 below. Tables 4-6 show the weight for each sample of SP-80A-150 IPA/water coated sponges.

TABLE 3 original sponge weight before coating with SP-80A-150

| Sample | Sponge weight |
| --- | --- |
| A | 3.97953 g |
| E | 4.09682 g |
| G | 4.19049 g |
| J | 4.61959 g |
| B | 4.11759 g |
| C | 4.08744 g |
| D | 4.12735 g |
| L | 4.09888 g |
| F | 3.77769 g |
| I | 4.56754 g |
| K | 4.09888 g |
| M | 4.34280 g |

TABLE 4 weight after first coat of SP-80A-150 IPA/water coated sponges

| Sample | 1st Coat weight |
| --- | --- |
| A | 5.24905 g |
| E | 5.31488 g |
| G | 5.1918 g |
| J | 6.08016 g |

TABLE 5 weight after second coat of SP-80A-150 IPA/water coated sponges

| Sample | 2nd Coat Weight |
|---|---|
| B | 5.812 g |
| C | 5.888 g |
| D | 5.783 g |
| L | 5.861 g |

TABLE 6 weight after third coat of SP-80A-150 IPA/water coated sponges

| Sample | 3rd Coat Weight |
|---|---|
| F | 5.6539 g |
| I | 6.6505 g |
| K | 6.5441 g |
| M | 6.1501 g |

The weight after the first coat was 5.4589 g on average. The weight after the second coat was 5.836 g on average. The weight after the third coat was 6.2133 g on average. The viscosity of the coating was 16,240 cP at 20% of torque used.

The sponge weight, prior to the coating, is shown in Table 7 below. Tables 8-10 show the weight of each sample after it was coated and heated at 90° C. for 1 hour.

TABLE 7 original sponge weight before coating with TG-500

| Sample | Sponge weight |
|---|---|
| ATG | 3.49637 g |
| BTG | 3.48642 g |
| CTG | 4.11879 g |
| DTG | 4.14722 g |
| ETG | 3.94106 g |
| FTG | 3.91135 g |
| GTG | 3.91137 g |
| HTG | 3.73683 g |
| ITG | 3.76910 g |
| JTG | 3.76787 g |

TABLE 8 weight after the first coat of TG-500 IPA/water coated sponges

| Sample | 1st Coat weight |
|---|---|
| ATG | 4.60042 g |
| BTG | 4.87432 g |
| CTG | 5.29062 g |
| DTG | 5.83271 g |

TABLE 9 weight after the second coat of TG-500 IPA/water coated sponges

| Sample | 2nd Coat weight |
|---|---|
| ETG | 5.2359 g |
| FTG | 5.47746 g |
| GTG | 5.62497 g |

TABLE 10 weight after the second coat of TG-500 IPA/water coated sponges

| Sample | 3rd Coat weight |
|---|---|
| HTG | 5.12392 g |
| ITG | 5.3869 g |
| JTG | 5.41773 g |

The weight after the first coat was 5.14952 g on average. The weight after the second coat was 5.44611 g on average. The weight after the third coat was 5.30952 g on average. The decrease in weight between the second coat and the third coat is likely due to the thin viscosity of the TG500 solution which caused a longer "tail" to form at the end of the sponge as the solution dripped from the previously coated sponge. The tail was removed before measuring the coating weight.

Samples coated with SP-80A-150 were studied to determine how much of the hydrogel coating was retained on the sample. The samples were able to retain more coating on the third dipping cycle than in the second. SP-80A-150 retains consistent coatings through the $2^{nd}$ and $3^{rd}$ cycles. Tables 11 shows the weight after the first coating and tables 12 and 13 show the retained weight after the second and third coating, respectively.

TABLE 11 weight after first coating with SP-80A-150 IPA/water mixture

| 1st Coat | Coating weight |
|---|---|
| A | 1.26952 g |
| E | 1.21806 g |
| G | 1.00131 g |
| J | 1.46057 g |

TABLE 12 retained weight after the second coating

| 2nd Coat | Coating weight | Retained coating (2) |
|---|---|---|
| B | 1.69405 g | 0.4432 g |
| C | 1.80056 g | 0.50581 g |
| D | 1.65565 g | 0.39091 g |
| L | 1.76212 g | 0.35524 g |

TABLE 13 retained weight after third coating

| 3rd Coat | Coating weight | Retained coating (2) | Retained coating (3) |
|---|---|---|---|
| F | 1.87616 g | 0.27044 g | 0.43585 g |
| I | 2.08294 g | 0.37680 g | 0.49448 g |
| K | 1.94916 g | 0.36250 g | 0.40910 g |
| M | 1.80729 g | 0.34234 g | 0.46109 g |

Samples coated with TG-500 were studied to determine how much of the hydrogel coating was retained on the sample. The solution had a much lower viscosity than the SP-80A-150. This caused tails to form on some of the samples. The tails were cut before being weighed. Tables 14 shows the weight after the first coating and tables 15 and 16 show the retained weight after the second and third coating, respectively.

TABLE 14 weight after first coating with TG-500 IPA/water mixture

| 1st Coat | Coating weight |
|---|---|
| ATG | 1.10405 g |
| BTG | 1.3879 g |
| CTG | 1.17183 g |
| DTG | 1.69549 g |

TABLE 15 retained weight after second coating

| 2nd Coat | Coating weight | Retained coating (2) |
|---|---|---|
| ETG | 1.29484 g | 0.29588 g |
| FTG | 1.56411 g | 0.31416 g |
| GTG | 1.7136 g | 0.35405 g |

TABLE 16 retained weight after third coating

| 3rd Coat | Coating weight | Retained coating (3) |
|---|---|---|
| HTG | 1.38709 g | 0.19718 g |
| ITG | 1.6178 g | 0.18657 g |
| JTG | 1.64986 g | 0.22477 g |

A suction catheter was cut into 4-8 inch lengths. 10-16 samples were made to collect multiple sets of data. Sponges were cut into appropriately sized rectangles. The sponges were then glued to the tubing with LOCTITE® 4013, an instant adhesive. These sponges were coated with the hydrogels by dip-coating.

The samples were placed into a conical tube to collect water absorption data. Conical tubes were filled with a recorded volume of water, and samples were cut down to fit inside the tubes. After 30 minutes, the samples were removed and the remaining water volume was recorded. Two repetitions were performed for each coat.

The samples coated with SP-80A-150 IPA/H$_2$O were ranked in order of most lubricious to least lubricious. The samples were ranked based on how slippery they felt after being removed from the test tubes. The samples in Table 17 below are ordered from most to least lubricious, with sample M being the most lubricious. Samples that had more coatings applied were more lubricious.

TABLE 17 water absorption for samples coated with SP-80A-150 IPA/H$_2$O

| Sample (# of coats) | mL H$_2$O absorbed | % H$_2$O absorbed* |
|---|---|---|
| M (3) | 11 mL | 36.67% |
| F (3) | 11 mL | 36.67% |
| B (2) | 17 mL | 56.67% |
| D (2) | 16 mL | 53.33% |
| G (1) | 14 mL | 46.67% |
| J (1) | 12 mL | 40% |
| H (0) | 16 mL | 53.33% |
| O (0) | 19 mL | 63.33% |

Figure 10:
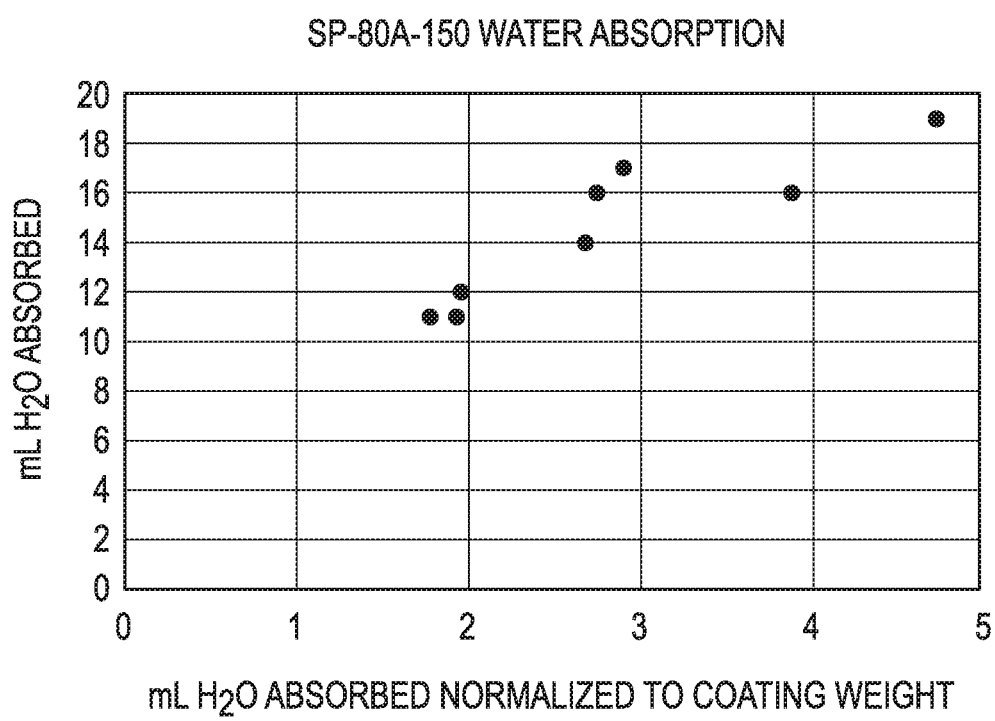
FIG. 10 is a graph showing the volume of water absorbed against the volume of water absorbed normalized to the coating weight, when the coating is SP-80A-150.

The percent of water absorbed in Table 17 and 18 is the percentage of water absorbed of the original 30 mLs of water that was originally introduced (not based on sponge weight). These absorption measurements were made without suction. FIG. 10 shows a graph of the water absorption for samples coated with the SP-8A-150. Increasing the number of coatings tended to reduce the percentage of water that was absorbed.

TABLE 18 the water absorption for samples coated with TG-500

| Sample (# of coats) | mL H$_2$O absorbed | % H$_2$O absorbed* |
|---|---|---|
| ATG (1) | 11 mL | 36.67% |
| BTG (1) | 13 mL | 43.33% |
| CTG (1) | 14 mL | 46.67% |
| DTG (1) | 14 mL | 46.67% |
| ETG (2) | 10 mL | 33.33% |
| FTG (2) | 11.5 mL | 38.33% |
| GTG (2) | 14 mL | 42.42% |
| HTG (3) | 11 mL | 36.67% |
| ITG (3) | 10 mL | 33.33% |
| JTG (3) | 10 mL | 33.33% |

Figure 11:
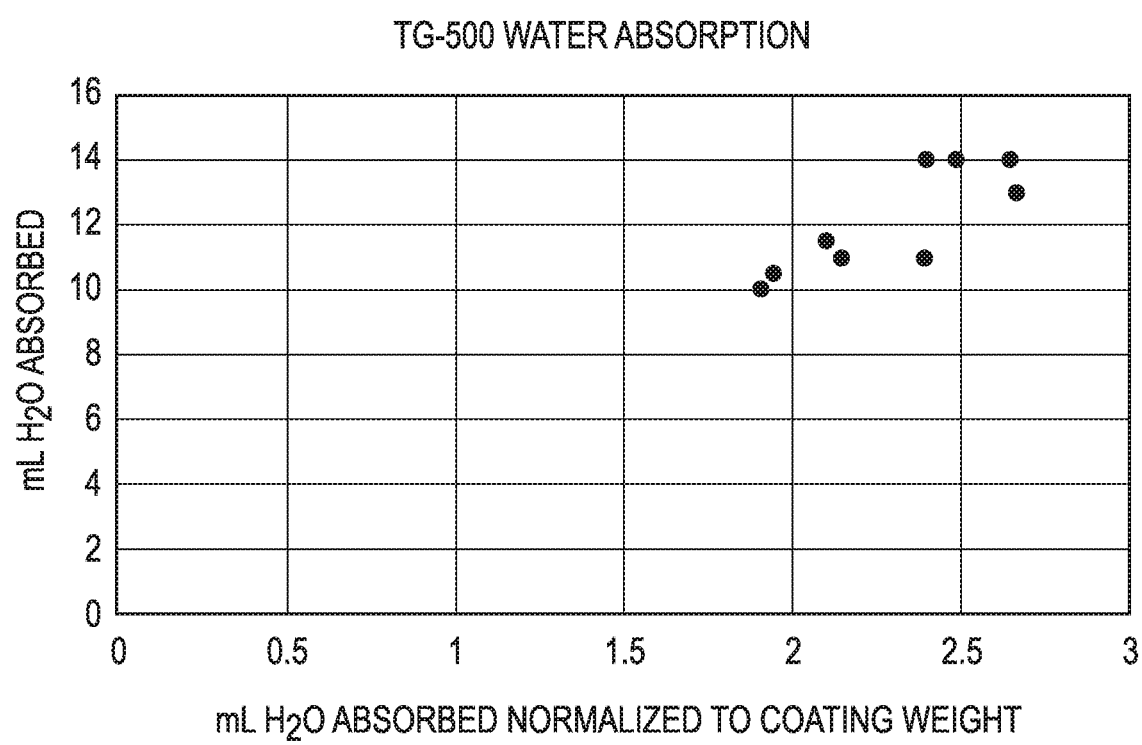
FIG. 11 is a graph showing the volume of water absorbed against the volume of water absorbed normalized to the coating weight, when the coating is TG-500.

FIG. 11 shows a graph of the TG-500 water absorption. Increasing the number of coatings tended to reduce the percentage of water that was absorbed.

REFERENCES

1. Sole, M. L., et al., "Oropharyngeal secretion volume in intubated patients: the importance of oral suctioning", *Am J Crit Care*, 20(6):141-45 (2011).
2. International Application, International Publication Number WO 92/007602.
3. German Patent No. DE 69126797.
4. International Applications, International Publication Number WO 95/23624.
5. International Applications, International Publication Number WO 99/38548.
6. International Applications, International Publication Number WO 2010/067225.
7. U.S. Pat. No. 7,465,847.
8. Maldonado-Codina, C., "Hydrogel lenses—materials and manufacture: a review" *Optometry in Practice*, 4: 101-15 (2003).
9. Jones et al., "Silicone hydrogel contact lens materials update" (July 2004), available online at www.siliconehydrogels.org/editorials/index_july.asp and www.siliconehydrogels.org/editorials/index_august.asp.
10. Benz Research & Development (BRD), "Advanced lens materials & manufacture technology", available online at www.benzrd.com/pdf/Advanced Lens Materials 08.pdf.
11. "Standard Test Method for Volatile Content of Coatings" ASTM International (https://www.astm.org/Standards/D2369.htm) viewed on Apr. 8, 2019.
12. "Plastics for Medical Use" Colorado Plastic Products (https://coloradoplastics.com/plastic-for-medical-use/) viewed on Jun. 12, 2019.

What is claimed is:

1. An oral suction device, comprising:
a suction catheter having a suction portion at a first end,
a sponge connected to the suction portion,
a porous non-hydrogel coating applied on the sponge, and
a suction tubing connector, on a second end of the suction catheter, opposite the first end.

2. The oral suction device of claim 1, wherein the non-hydrogel coating is a silicone coating.

3. The oral suction device of claim 1, wherein the non-hydrogel coating is a polymer coating.

4. The oral suction device of claim 1, wherein the sponge is radiopaque.

5. The oral suction device of claim 1, wherein the suction portion has a length of 2.5 to 30 cm.

6. The oral suction device of claim 1, wherein the oral suction device is sterile.

7. The oral suction device of claim 1, further comprising a retention connector attached to the suction catheter.

8. The oral suction device of claim 7, wherein the retention connector is a C-clip.

9. The oral suction device of claim 1, wherein one of the coating and the sponge is impregnated with an antibiotic.

10. The oral suction device of claim 9, wherein the antibiotic is at least one member selected from the group consisting of cephalosporines, fluoroquinolones, β-lactams, carbapenems, glycopeptides and aminoglycosides.

11. The oral suction device of claim 1, wherein the sponge has an expanded figure-8 shape.

12. The oral suction device of claim 1, wherein the sponge has a length of 5 to 25 cm, a width at a widest point of 3 to 8 cm, a width at a narrowest point of 2 to 7 cm, and a height of 0.3 to 4 cm.

13. The oral suction device of claim 1, further comprising a vacuum lock relief tube inside the suction catheter, wherein the vacuum lock relief tube creates a gas pathway from atmosphere outside the suction catheter into the sponge or shell.

14. The oral suction device of claim 1, further comprising an esophageal stethoscope and an electronic temperature probe.

15. The oral suction device of claim 14, further comprising a lead tube, wherein one or more leads located within the lead tube are in electrical communication with the temperature probe.

16. The oral suction device of claim 15, wherein the leads are connected to a lead adaptor.

17. The oral suction device of claim 1, further comprising an esophageal stethoscope and an electronic temperature probe, wherein the esophageal stethoscope comprises a stethoscope tube having a listening end.

18. The oral suction device of claim 17, wherein the stethoscope tube is located within the suction catheter.

19. The oral suction device of claim 17, wherein a seal separates the listening end of the esophageal stethoscope from the suction portion.

20. An oral suction device, comprising:
a suction catheter having a suction portion at a first end,
a sponge connected to the suction portion,
a porous non-hydrogel coating applied on the sponge, wherein the non-hydrogel coating is one of a silicone coating and a polymer coating and defines a plurality of holes having an average diameter greater than 0.1 mm, and
a suction tubing connector, on a second end of the suction catheter, opposite the first end.

* * * * *